United States Patent [19]
Rollén

[11] Patent Number: 5,603,896
[45] Date of Patent: Feb. 18, 1997

[54] METHOD AND MEANS TO BRING ABOUT AND MAINTAIN A MICROBIOLOGICALLY CLEAN ENVIRONMENT IN ROOMS

[76] Inventor: Jarl-Erik Rollén, Magnebergskroken 5, S-122 31, Enskede, Sweden

[21] Appl. No.: 647,202

[22] Filed: May 9, 1996

Related U.S. Application Data

[63] Continuation of Ser. No. 244,259, filed as PCT/SE92/00763, Nov.5, 1992, abandoned.

[30] Foreign Application Priority Data

Nov. 21, 1991 [SE] Sweden .................................. 9103418

[51] Int. Cl.$^6$ .......................... A61L 2/16; A01N 25/24; C09D 5/00
[52] U.S. Cl. ..................... 422/28; 424/407; 424/412; 427/403; 106/15.05
[58] Field of Search .......................... 422/1, 28; 424/405, 424/407, 412; 427/155, 403, 2.1, 397.7, 397.8; 106/15.05, 18.32, 18.35

[56] References Cited

U.S. PATENT DOCUMENTS

| 4,122,192 | 10/1978 | Fellows | 424/333 |
|---|---|---|---|
| 4,225,361 | 9/1980 | Joseph | 106/111 |
| 4,391,859 | 7/1983 | Fogelberg | 427/421 |
| 4,394,378 | 7/1983 | Klein | 424/184 |
| 4,442,242 | 4/1984 | Fogelberg | 523/200 |
| 4,654,368 | 3/1987 | Sakamoto et al. | 514/493 |
| 4,900,736 | 2/1990 | Diehl | 514/245 |
| 5,242,893 | 9/1993 | Willingham | 504/138 |

FOREIGN PATENT DOCUMENTS

| 498213 | 1/1977 | Australia . |
| 03-177796 | 8/1991 | Japan . |

*Primary Examiner*—Robert J. Warden
*Assistant Examiner*—E. Leigh Dawson
*Attorney, Agent, or Firm*—Watson Cole Stevens Davis, P.L.L.C.

[57] ABSTRACT

A method for establishing and maintaining a microbiologically clean environment in a room by painting at least its wall and ceiling surfaces with a porous layer formed of a porous material, such as perlite, zeolite or micronized silicon dioxide, optionally mixed with a fungicide or bactericide, then repeatedly spreading an aqueous liquid mixture containing a sanitizer over the porous layer, the water in the aqueous liquid mixture being evaporated between each application, leaving sanitizer in the pores of the porous layer.

4 Claims, No Drawings

METHOD AND MEANS TO BRING ABOUT AND MAINTAIN A MICROBIOLOGICALLY CLEAN ENVIRONMENT IN ROOMS

CROSS REFERENCE TO RELATED APPLICATION

This application is a continuation of application Ser. No. 08/244,259, filed May 20, 1994, now abandoned, which derived from International application no. PCT/SE92/00763, filed 5 Nov. 1992.

TECHNICAL FIELD

The present invention concerns a method and a means to bring about and maintain a micro-biologically clean environment in room by coating the wall surfaces and any other surfaces in a room with a composition of materials and then treating the coating.

BACKGROUND OF THE INVENTION

Activities with high requirments for hygiene e.g. food industries, hospitals, laboratories etc., are regularly cleaned by different types of sanitizers. The demands on hygiene also lead to is laid stress is laid on the materials which are used as linings in ceilings, walls and floors. The predominant is that only hard, smooth and non-porous materials should be used on surfaces in such rooms. If possible, tiles stainless plate, epoxy paints should be used, but by reason of costs, also simplier indoor paints such as bright latex paints, oil and alkyd paints, etc., are used. These materials are simple to wash from visible contaminants but have considerable drawbacks from the viewpoint of sanitation. It is a known but disregarded fact that painted surfaces in a room never can be completely diffusion tight. Also during the application of the paint layer craters and pores arise, and when the paint is aged, cracks arise. Additionally, the equipment in the room require that screws, nails, pipes, cables, ventilation ducts, etc., be attached to and brought through the painted surfaces.

Food industries as a rule have a high air humidity. The vapour pressure in a room as a rule is higher than in the surrounding ceilings, walls and floors. Consequently a diffusion of vapour occurs in all openings in the painted coating of the surface (also microscopical), during which the vapour condenses in the wall behind the coating of the surface. The condensed vapour which is transferred into a liquid state cannot in the same easy way move back through the tight coating of the surface as the vapour pressure in the room drops. The walls in rooms with a high air humidity as a rule contain an excess of humidity. This humidity makes a good condition for the growth of micro-organisms and in humid locations this growth behind the paint layers is a problem.

The rooms are daily, i.e., cleaned floors, walls and equipment are washed with a high pressure washer, after which the surfaces, which are to be kept free from micro-organisms, are treated with a sanitizer. During this sanitation the major part of the sanitizers which are sprayed upon walls and ceilings quickly flow away and evaporate from the surface. As the sanitizers only are active in a liquid state, the time in which they affect the micro-organisms is proportionately short and the efficiency consequently will be very low. Besides, the sanitizer will only reach the micro-organisms on the outside, whereas micro-organisms located behind the coating are protected. The surface thus is re-infected not only by micro-organisms in the air in the room but above all by micro-organisms remaining on the back of the paint layer. When the activity of the sanitizer has ceased, the micro-organisms penetrate from the growing locations on the back of the paint layer, which explains why the visible or measurable re-infection sometimes will be surprisingly quick. The re-infection often takes place in a shorter time than 24 hours after the sanitation. This is a problem as most industries have difficulties in carrying out more than one sanitation every 24 hours.

Porous materials traditionally have been regarded as completely unsuitable in rooms with high demands on hygiene. They are regarded as difficult to clean, attracting contaminants and micro-organisms and a good growing base for bacteria, mould, algae, fungi etc.

During laboratory tests and full-scale tests it has now surprisingly been proved that certain types of porous paints have a considerably better resistance to micro-organisms than stainless steel plate. Tests also surprisingly have proved that these types of porous materials are easier to sanitize than corresponding smooth surfaces. Such a porous material is described in the Swedish Patent Publication SE-C-387 681, by which it is also known to prevent or lower the presence of condensate on a surface with a layer of a porous composition of materials including granules with adsorbing and desorbing qualities. This composition of materials also has good heat insulating qualities, which means that a layer of this composition maintains a little higher temperature than a corresponding smooth surface in one and the same room. As a consequence, the porous composition of materials do not attract dust and contamination from the air to the same extent as a smooth surface.

SUMMARY OF THE INVENTION

The object of the present invention is to provide a method and means to establish and maintain a micro-biologically clean environment in rooms in which an activity with strict hygiene restrictions is to take place. The object is achieved by a method wherein ceilings, wall surfaces and eventually other surfaces in a room, after a preceding sanitation is coated with a layer of a composition of materials which is porous, open for diffusion and prevents condensation, including granules of organic or expanded inorganic materials and binders, and wherein a water soluble sanitation liquid is spread on the layer of the porous composition of materials at repeated intervals of time, and wherein as the water in the sanitation liquid is evaporated a sanitizer remains in the pore system of the composition of materials. The means for to accomplishing the method according to the invention is characterized in that it comprises a porous, moisture-adsorbing and condensate-preventing composition of materials including granules of organic or expanded inorganic materials and a water soluble sanitation liquid which is spread upon the composition of materials and which, as the water in the same is evaporated, remains as a sanitizer, preferably as a vapour, and/or in a solid state in the pore system of the composition of materials. Preferably the composition of materials includes one or more porous materials such as perlite, zeolite, bentonite, micronized silicon dioxide or christobalite. The composition of materials also can include one or more materials with the capability to take up water molecules directly from the surrounding air, such as salts, silicon dioxide gel, starch or compounds of cellulose, gypsom, alkali silicate, aluminium silicate or fullers earth. The composition of materials also can include one or more water-insoluble fungicides and bactericides such as N-arylamide, alkyl-arylsulfonic acid, octylisothiazolinone, chloromethyl-isothiazolinone, methylisothiazolinone, iodinated alkyn-alkylkarbamate, 1,2-benzisothiazol-3(2H)-one separately or in different combinations.

During sanitation of a porous composition of materials according to the invention a sanitation liquid comprising a sanitizer is sprayed, painted or otherwise brought to spread in the pore system of the composition of materials. The sanitation liquid is absorbed by means of capillary forces in the porous composition of materials and equally distributed over all of the surface coated with the actual composition of materials. After spreading of the sanitation liquid mainly the water in the same evaporates, and the sanitizer by a good surface adhesion remains in the pore system of the composition of materials. The evaporation of the water from the composition of materials is intensified insofar as the pore system substantially enlarges the coated surface and the composition of materials by its heat insulating capability maintains a higher temperature than a corresponding smooth, painted surface. Sanitizers such as didecyl dimethyl ammoniumchloride, sodium ortho fenylfenate tetrahydrate, glutaraldehyde, chloromethylisothiasolinione separately or in different combinations have a capability to of dissolving the walls of the cells of the micro-organisms, such that water penetrates into the cells which are exploded. As such, the sanitizers also lower the surface tension in the pore system and the water will leave this system faster compared with a pore system only containing water. The sanitizer first mentioned also has an antistatic effect, which lowers the possibilities for the micro-organisms to get caught on the coated surface.

A concentration of the sanitizers in water preferably is 150 to 500 ppm and is gradually increased in this interval at subsequent sanitations. After a certain number of sanitations with one and the same sanitizer, the micro-organisms become resistant despite higher concentrations, so the sanitizer must be changed. As resistance also is commenced for the second sanitizer, it will be possible to return to the first sanitizer to which the micro-organisms are no longer resistant. Normal intervals for the change of sanitizer is four months, but tests indicate that the intervals can be extended by the efficiency of the invention.

By the invention the following effects are reached:

1. The composition of materials keeps the surface dry for longer periods by its capability of preventing condensation during normal production conditions than a smooth, tight surface. When the surface is dry no microbiological activity takes place.

2. The pore system of the composition of materials is more finely porous than a normal wall of concrete, B brick or plaster. The capillary forces will adhere eventual condensate in the wall material, which decreases the conditions for a micro-biological activity in the wall itself.

3. The composition of materials is open for diffusion and allows a diffusion of vapor without restrictions in both directions also from the building material behind.

4. When the sanitation liquid is spread on the composition of materials it is distributed by means of the capillary forces all over the entire surface layer and penetrates into the building material therebeneath. Thus, a deep sanitation is achieved.

5. At a thickness of the coating of 1 mm the composition of materials has a capability to adsorb and keep ½–1 litre of sanitation liquid per m$^2$ which is considerably more than what is normally used in sanitation. All sanitation liquid will be used and will be given a possibility to act during a sufficient period of time in order to effectively kill all micro-biological life in and on the surface layer.

6. As the sanitation liquid evaporates, the active substance, e.g. the sanitizer, which has a good surface adhesion, will be caught on the walls in the pore system of the composition of materials. In a dry condition, when normal micro-biological activity is impossible, the sanitizer is inactive. As the composition of materials will be humid again the sanitizer again will be activated. In this way the effect of the sanitizer will be very durable.

7. By interaction between the composition of materials and the sanitation liquid the concentration of the sanitizer can be kept very low. Thus, it will last a longer time than for traditional sanitation methods before the economic degree of concentration must be exceeded and a sanitizer with another way of acting must be used. This reality makes the method cost effective as well as lenient for the environment relative to common sanitation methods.

8. The insulating and condensation-preventing effect of the composition of materials as well as the anti-static characteristics of the sanitation liquid work against re-contamination as well as re-infection of the surface.

During a laboratory test re-infection of a smooth, painted surface was compared with a surface coated with the porous composition of materials according to the invention. The test surfaces firstly were sanitized with the same kind of sanitation liquid, after which they were dried. After that, the test surfaces were infected by organic material from dead animal bodies, after which they were kept in a climate chamber with alternating temperature and air humidity. Sampling each third hour showed a micro-biological growth on the smooth, painted test surfaces, within 24 hours, whilst the test surfaces coated with the porous composition of materials according to the invention were intact more than 7 days and nights.

I claim:

1. A method for establishing and maintaining a microbiologically clean environment in a room defined by wall and ceiling surfaces, said method comprising the steps of (a) painting wall and ceiling surfaces defining a room with a porous layer of a combination of first and second constituents, said first constituent being a porous material selected from the group consisting of perlite, zeolite, bentonite, micronized silicon dioxide and christobalite, and said second constituent being at least one fungicide or bactericide selected from the group consisting of N-arylamide, alkylarylsulphone acid, chloromethylisothiazolinone, methylisothiazolinone, iodinated alkyne-alkyl-carbamate, and 1,2-benzisothiazol-3(2H)-one, (b) spreading an aqueous liquid mixture containing a sanitizer over said porous layer at repeated intervals, and (c) evaporating the water from each application of the aqueous liquid mixture, leaving said sanitizer in pores of the porous layer.

2. A method according to claim 1, wherein step (b) comprises spreading a first acqueous liquid mixture containing a first sanitizer over the porous layer, and 1 to 12 months thereafter, spreading a second aqueous liquid mixture containing a second sanitizer over the porous layer.

3. A method according to claim 1, wherein said porous layer further includes a hydrophilic material selected from the group consisting of salts, silicon dioxide gel, starch, compounds of cellulose, gypsum, alkali silicate, aluminum silicate and fuller's earth.

4. A method according to claim 1, wherein said sanitizer is selected from the group consisting of didecyl dimethyl ammoniumchloride, sodium ortho fenylfenate tetrahydrate, glutaraldehyde, and chloromethylisothiazolinone.

\* \* \* \* \*